United States Patent [19]

Addy et al.

[11] 4,248,165
[45] Feb. 3, 1981

[54] METHOD AND APPARATUS FOR SEWING A COVER UPON A BALL CORE

[76] Inventors: Clarence A. Addy, 3128 Elmer St.; William C. Krizen, 2811 New England, both of, Sarasota, Fla. 33581

[21] Appl. No.: 95,875

[22] Filed: Nov. 19, 1979

[51] Int. Cl.³ .............................................. D05B 3/00
[52] U.S. Cl. ............................ 112/121.28; 112/171; 112/262.1; 112/262.3; 112/269.1
[58] Field of Search ................... 112/121.28, 170, 171, 112/172, 94, 262.1, 269.1, 262.3, 2

[56] References Cited

U.S. PATENT DOCUMENTS

| | | | |
|---|---|---|---|
| 515,713 | 2/1894 | Miller | 112/171 |
| 954,443 | 4/1910 | Larsen | 112/171 |
| 1,523,535 | 1/1925 | Eberhardt | 112/94 |
| 2,976,827 | 3/1961 | Bauder, Jr. | 112/121.28 |
| 3,179,075 | 4/1965 | Fossa | 112/121.28 X |

*Primary Examiner*—H. Hampton Hunter
*Attorney, Agent, or Firm*—John J. Byrne

[57] ABSTRACT

A method and apparatus for sewing cover halves together around a baseball core or the like. The method includes the steps of advancing first and second needles in one direction over an edge of a first cover half and under and through an edge of an adjacent second cover half. The needles carry first and second double threads through the second over half. The ball cover is then indexed forward and the first and second needles are advanced in an opposite direction over the edge of the second cover half and under and through the edge of the first cover half for carrying the first and second threads over the edge of the second cover half and through the edge of the first. Prior to the second step of advancing, the second thread is positioned between the first and second needles and above the first needle so that a regular herringbone stitch pattern between the first and second cover halves is achieved as the steps are sequentially repeated. The apparatus includes first and second needles and means for shuttling the needles in parallel, and abreast, back and forth over and under and through opposing over halves. During every other shuttle motion a tab means holds the second thread between the needles and raised the thread above the first needles so as to create a regular herringbone stitch pattern between the first and second cover halves.

21 Claims, 38 Drawing Figures

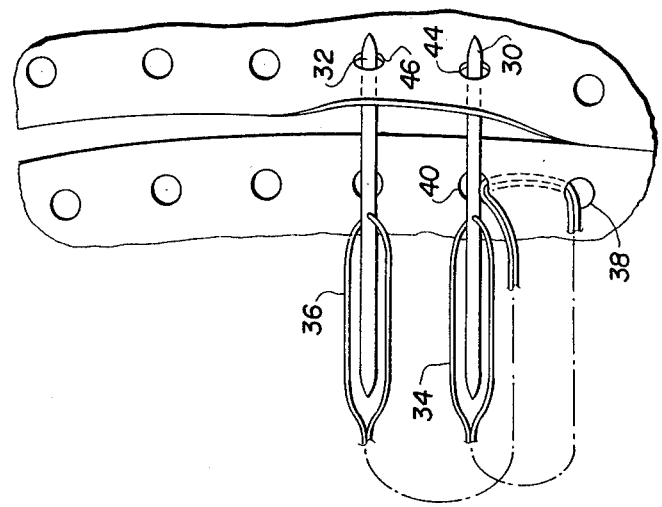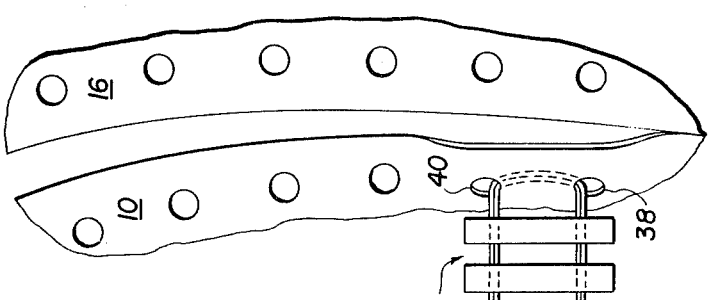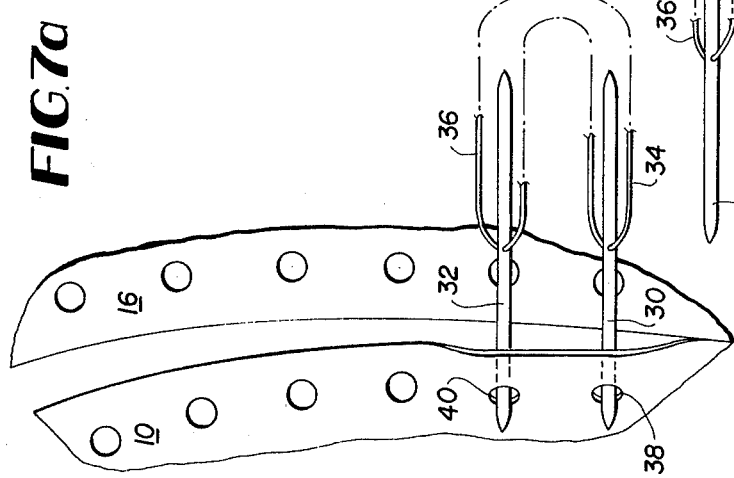

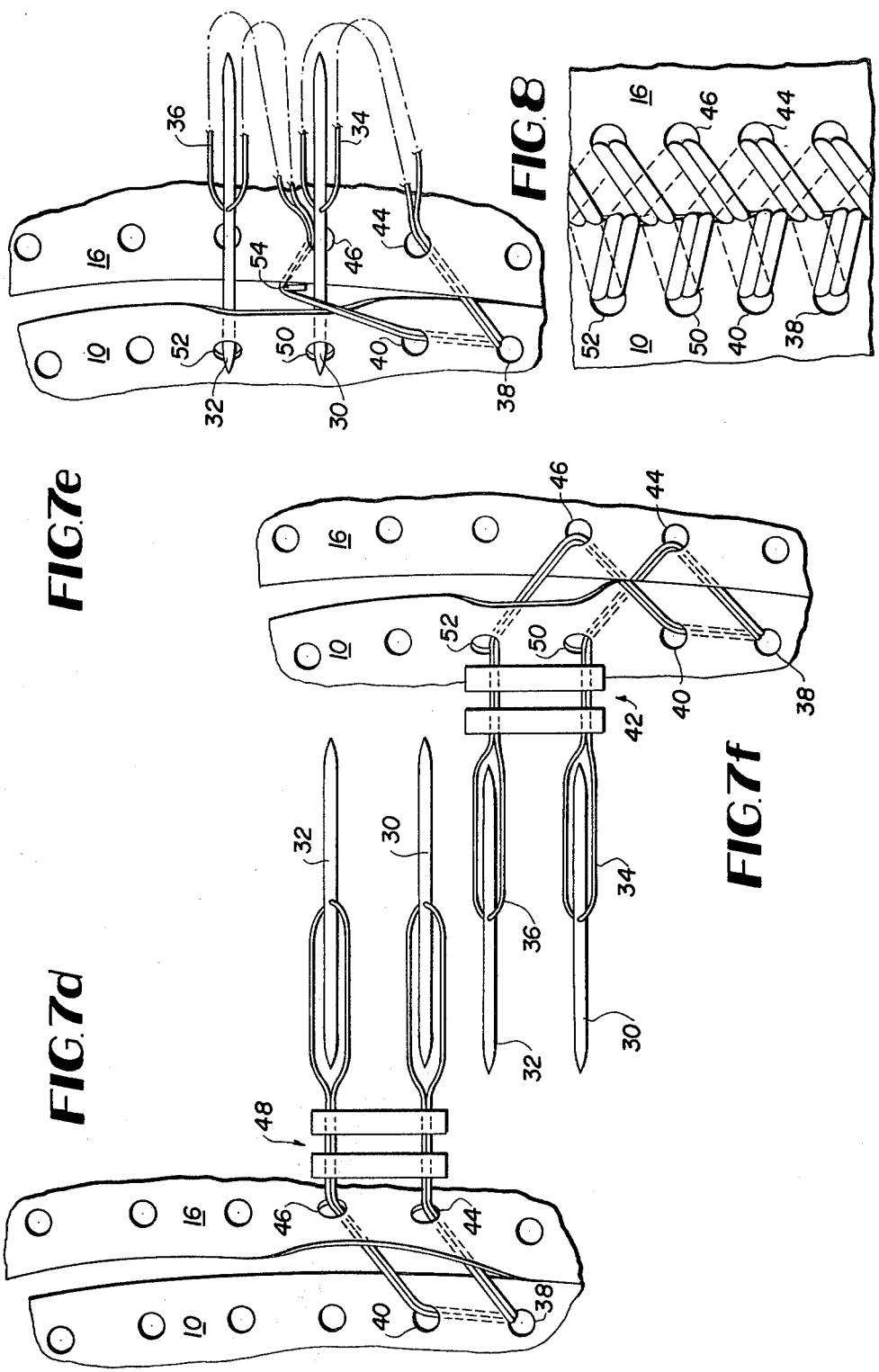

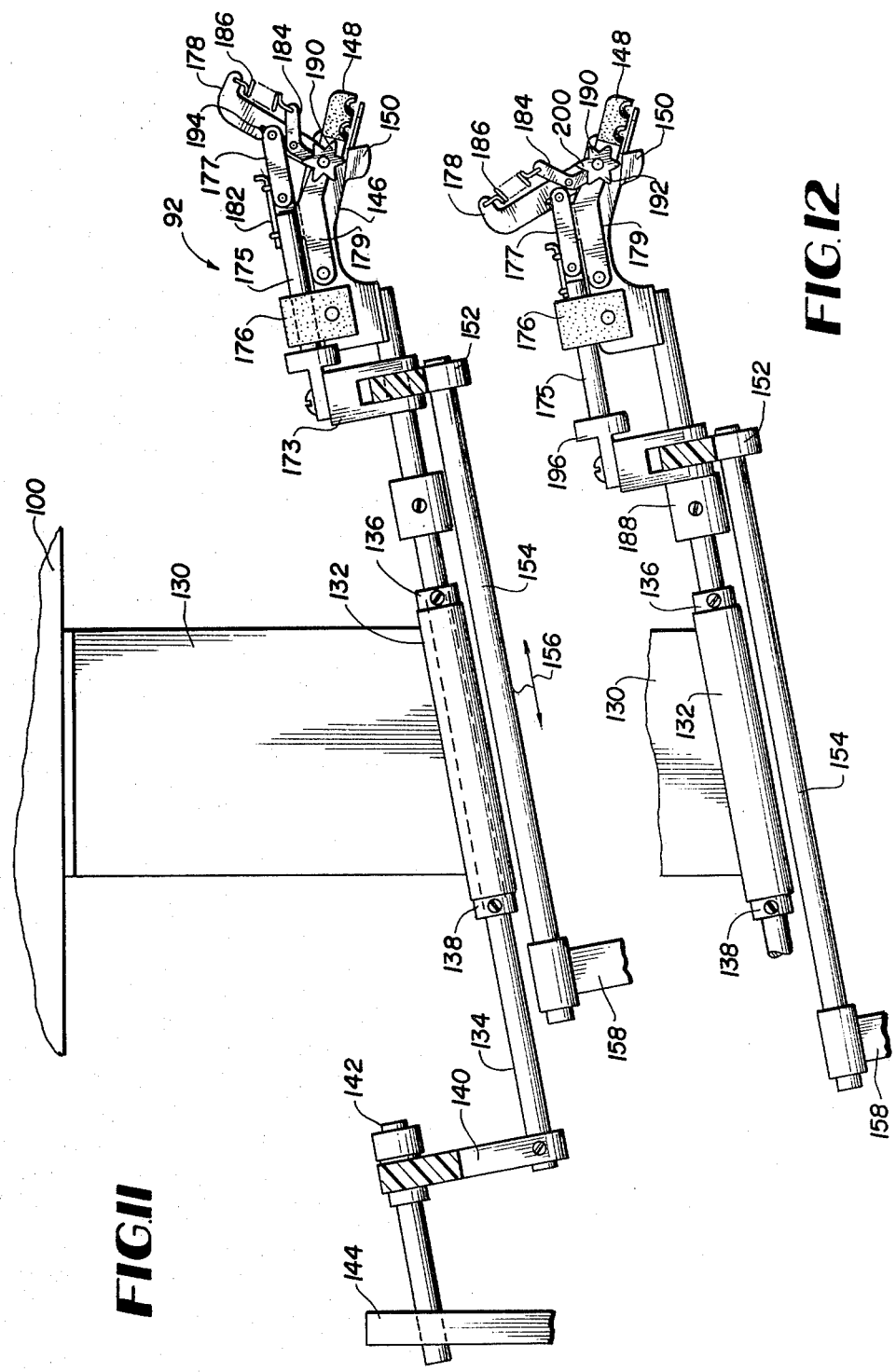

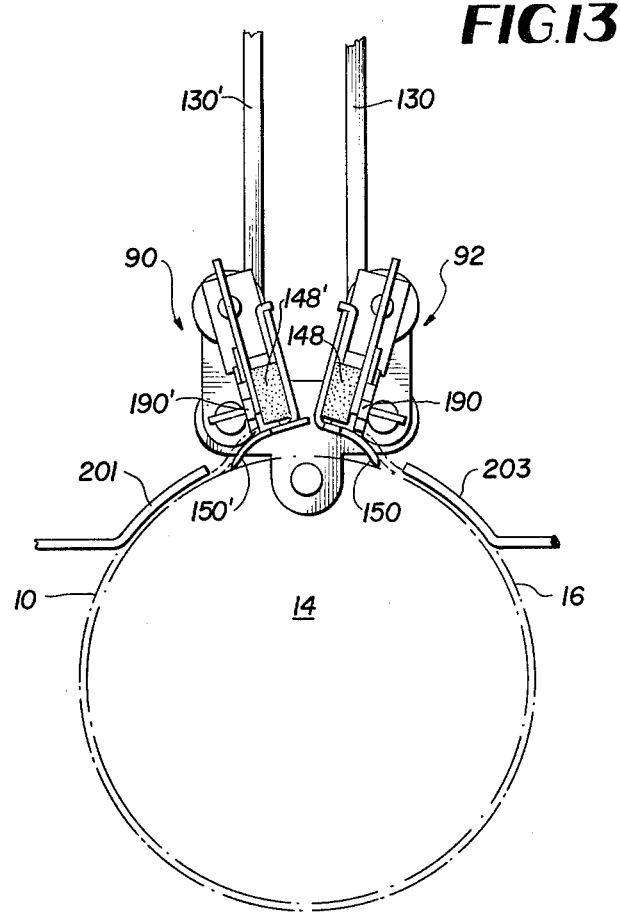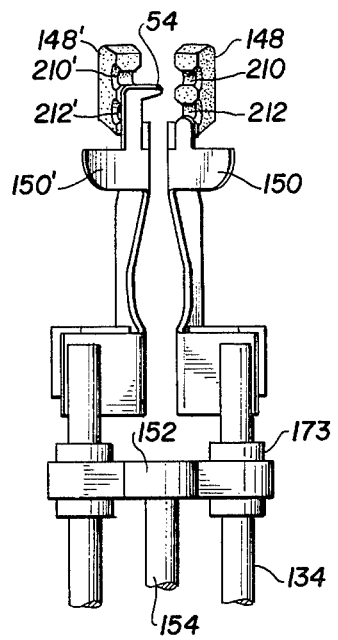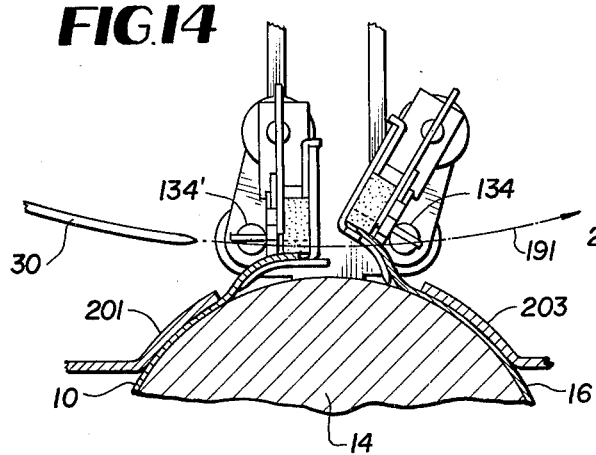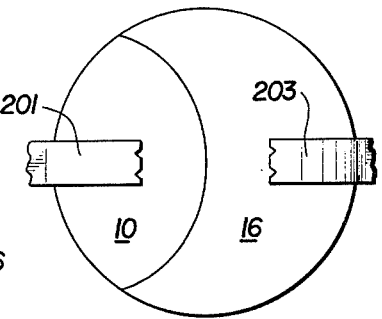

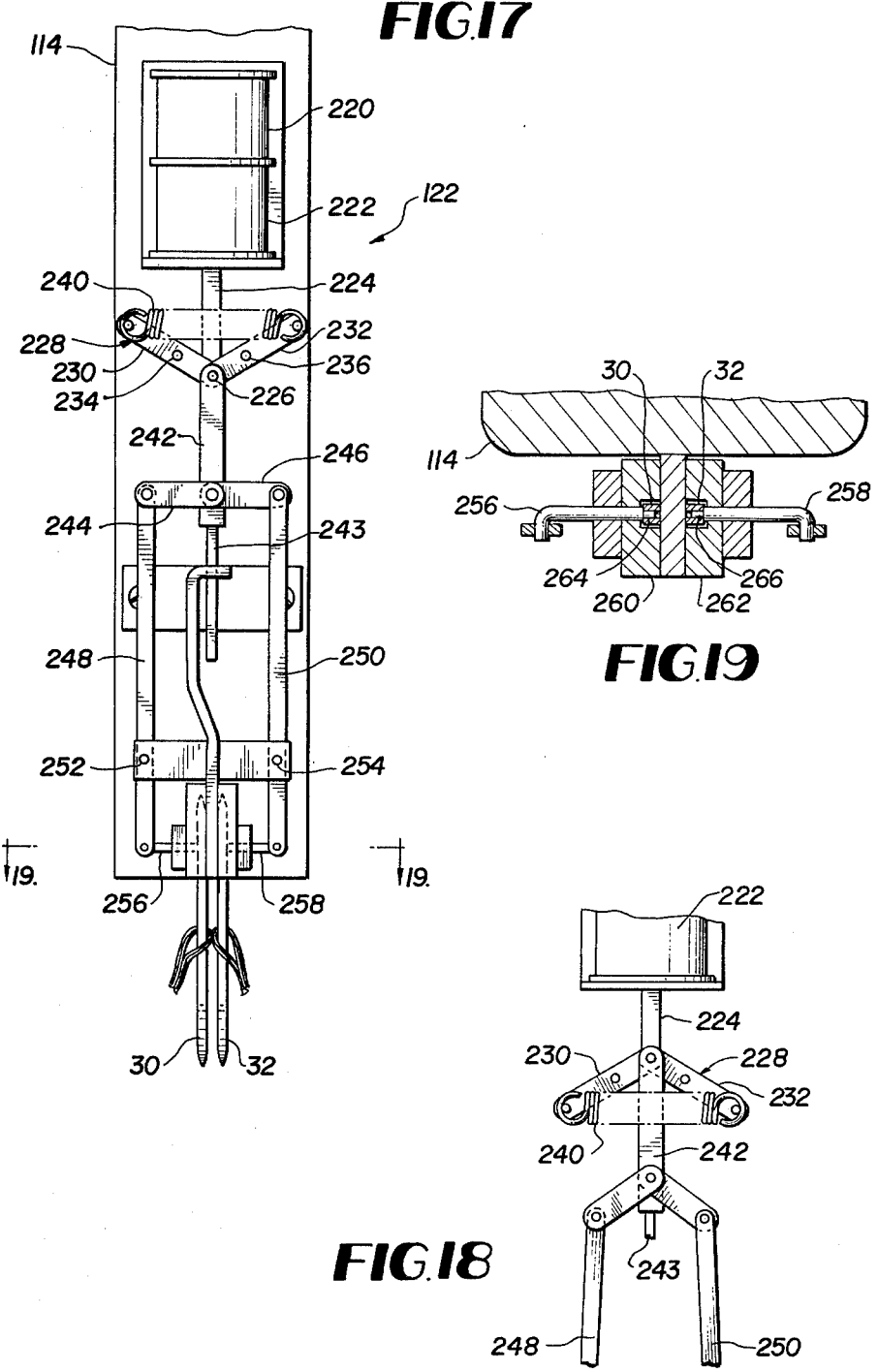

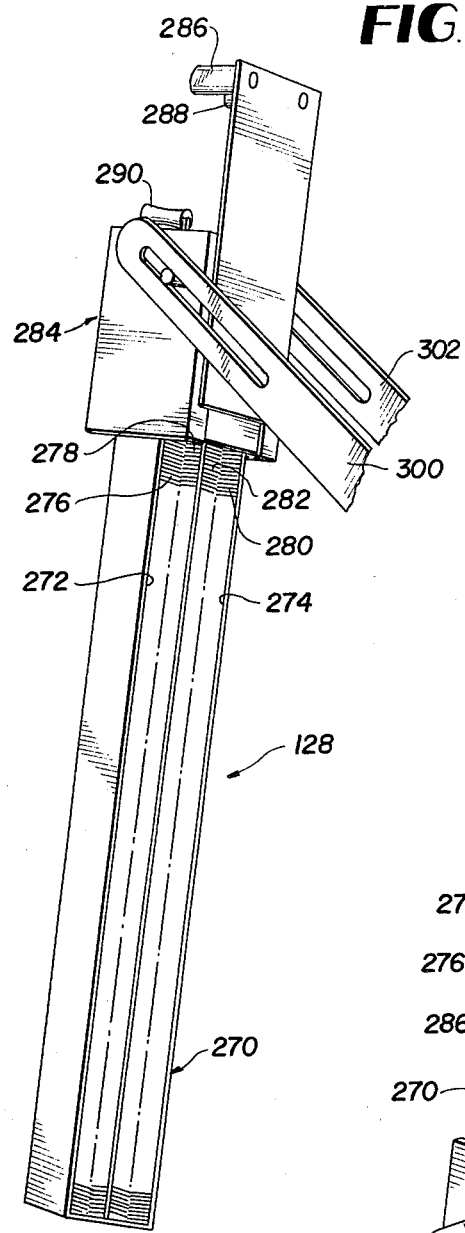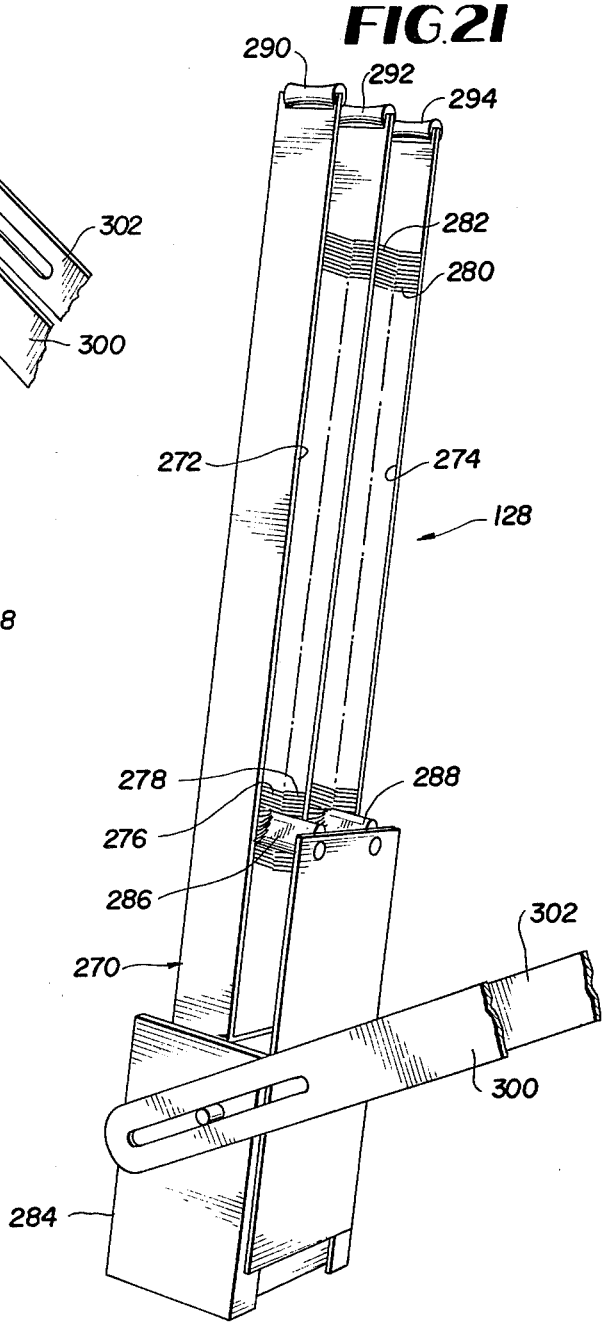

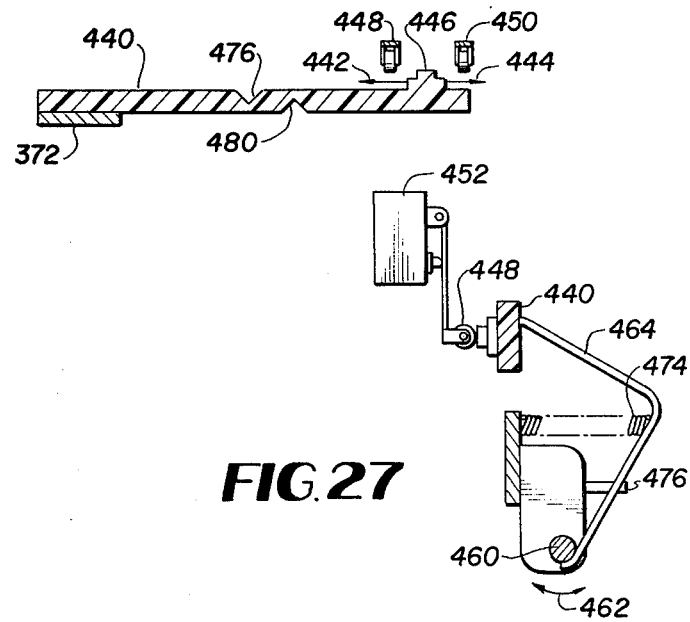
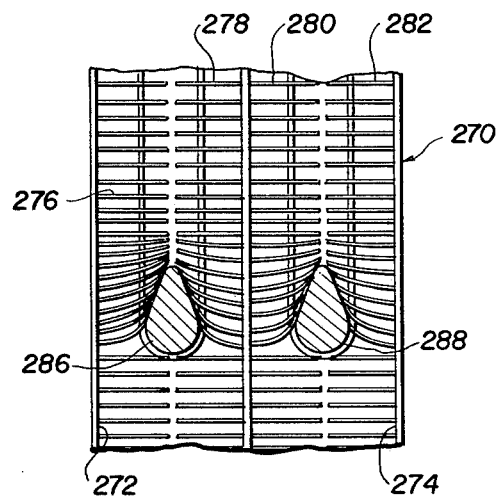

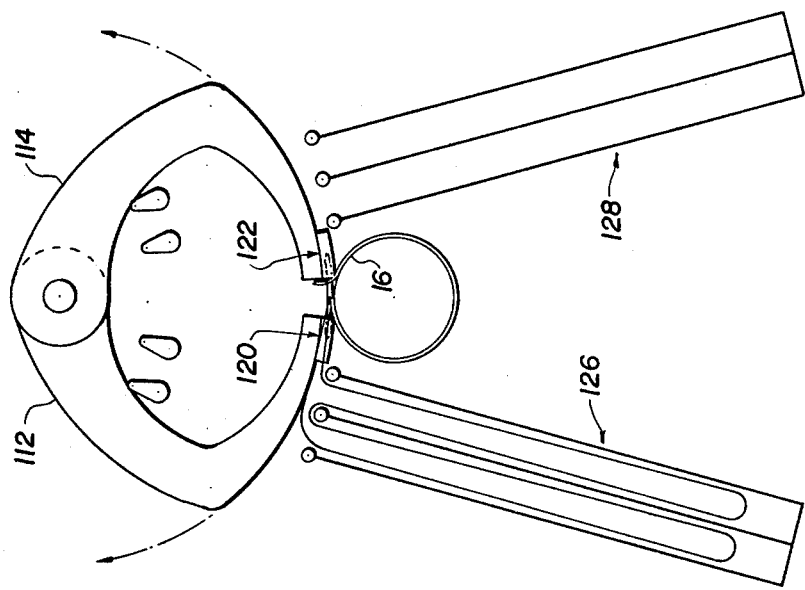
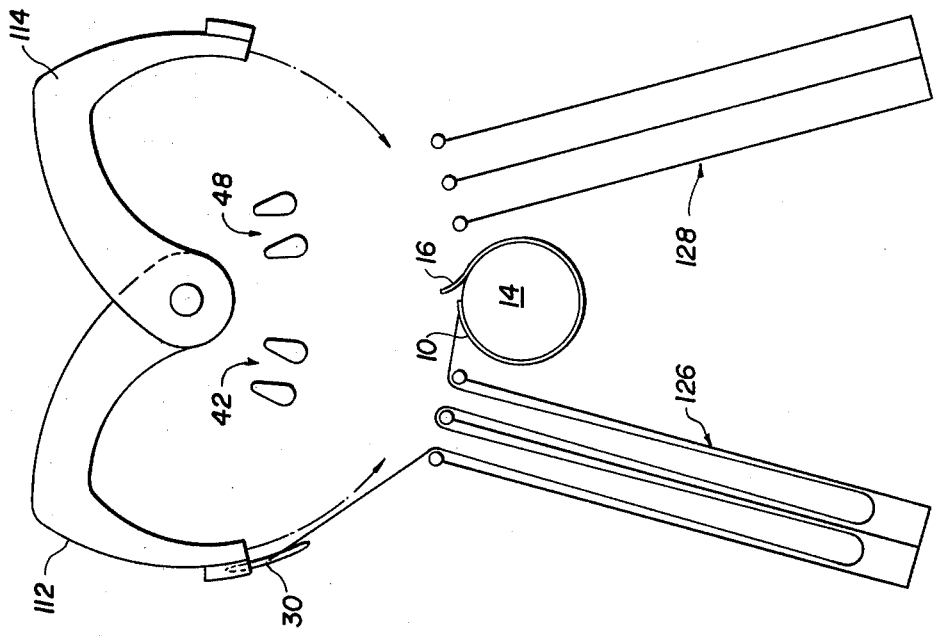

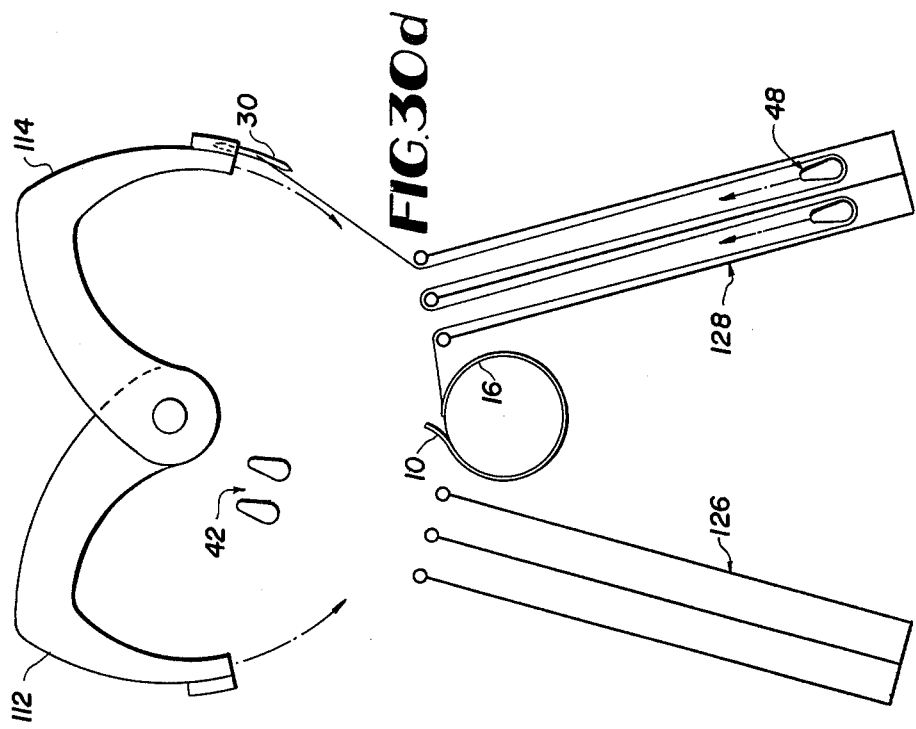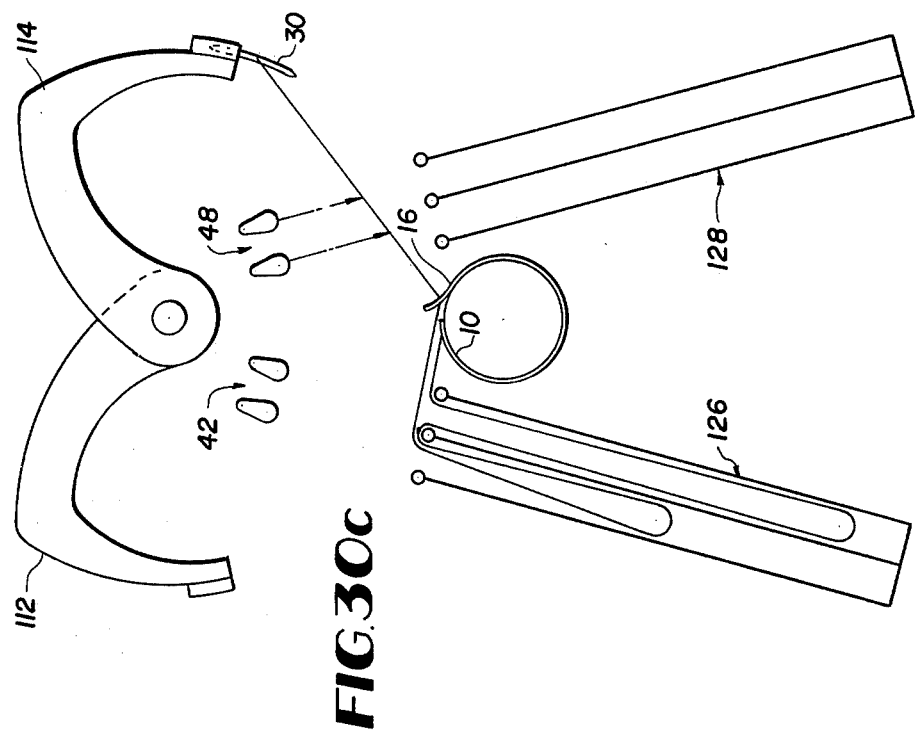

METHOD AND APPARATUS FOR SEWING A COVER UPON A BALL CORE

BACKGROUND OF THE INVENTION

This invention relates to a method and apparatus for sewing cover halves on a ball core. More specifically, the invention comprises a method and apparatus for stitching elliptical lemniscate halves of a ball cover around a core.

The construction of softballs, baseballs, and the like, as established by regulation and tradition, comprises the formation of a spherical foundation which is then wrapped with a continuous random overlay of elastic strand to form a ball core. The external dimensions of the ball core are maintained uniformly within narrow tolerances. A leather covering is then applied to the core in the general configuration of two bilobate pieces fitted about the ball core with the interconnecting section of one piece disposed in a posture with its edges abutting the lobes of the other half.

Traditionally stitching is provided to fasten the edges of the cover halves together and to draw them uniformly and neatly into abutment. The exposed threads of the stitching forms a seam of herringbone configuration centered along the line of abutment of the cover edges. More specifically each exposed thread of the seam passes over and under an opposite abutting edge of a cover place. Moreover each thread is doubled to provide greater strength without additional thickness. By this stitching technique the edges of the cover pieces or halves are drawn snugly against each other to provide a spherical close fitting cover without exposure of the core or the edges of the cover halves. This results in a comparatively smooth and uniform ball.

Initially the stitching of baseballs and the like was performed by a hand operation. Hand stitching, however, is highly labor intensive and rapidly was targeted as one of the most expensive and time consuming aspects of the ball manufacturing operation.

Various elements in the industry theorized that machine sewing baseballs and the like would be desirable and it is believed that others have tried extensively to achieve a mechanized method and apparatus which would be capable of performing a ball stitching or sewing operation. The ball industry in general, and particularly the baseball industry and major leagues, however, have demanding regulations and standards which previously known ball stitching machines have been unable to meet. In this connection baseballs and the like require a double herringbone stitch with the "V" or vertex of the stitch directly over the seam line. The thread pairs must be uniform and regular without twisting of adjacent threads. The ball cover halves must be stretched tightly over the ball core and no space between the abutting edges of the cover halves along the seams is permitted. Additionally the stitch holes must be sharply defined without evidence of any pulling or tearing or other leather surface damage. Moreover the leather surface of the cover halves must be free of any grease, oil or any other residue which might impair the playability of the end product.

The foregoing stitch pattern, uniformity and quality requirements for official baseballs and the like have rendered previously known machines unacceptable and useless to the industry. As a consequence, it is believed that all major league baseballs are presently hand sewn in a labor intensive manner which has been known for decades.

OBJECTS OF THE INVENTION

It is therefore a general object of the invention to provide a novel method and apparatus for machine sewing a ball cover around a ball core which will meet the demands of the baseball industry.

It is another object of the invention to provide a novel method and apparatus for sewing cover halves about a ball foundation wherein the production rate may be greatly enhanced with respect to presently utilized hand sewing techniques.

It is a further object of the invention to provide a novel method and apparatus for sewing a ball cover upon a core wherein the conventional double stitch herringbone pattern is achieved.

It is a related object of the invention to provide a novel method and apparatus for machine sewing a ball cover upon a core wherein the conventional herringbone stitch pattern is applied with the V-shape of the stitching directly above the ball seam.

It is a further object of the invention to provide a novel method and apparatus for sewing ball cover halves upon a core wherein the stitching is uniformly tensioned throughout the ball seam to bring the cover edges into uniform mutual abutment.

It is still another object of the invention to provide a novel method and apparatus for sewing ball cover halves around a foundation or core wherein the sewing operation may be achieved without imparting mars, slits, or foreign substances to the smooth leather cover surface.

It is still further an object of the invention to provide a novel baseball sewing method and apparatus which quickly and efficiently sews baseball cover halves around a baseball core with the rapidity, uniformity and accuracy necessary to economically minimize the need for hand sewing operations while concomitantly meeting the demanding standards of the baseball industry.

It is yet another object of the invention to provide a novel method and apparatus for sewing cover halves around a ball core which will permit a single operator to monitor and control several ball sewing operations simultaneously.

THE DRAWINGS

Other objects and advantages of the present invention will become apparent from the following detailed description of a preferred embodiment thereof taken in conjunction with the accompanying drawings wherein.

Figure 9:
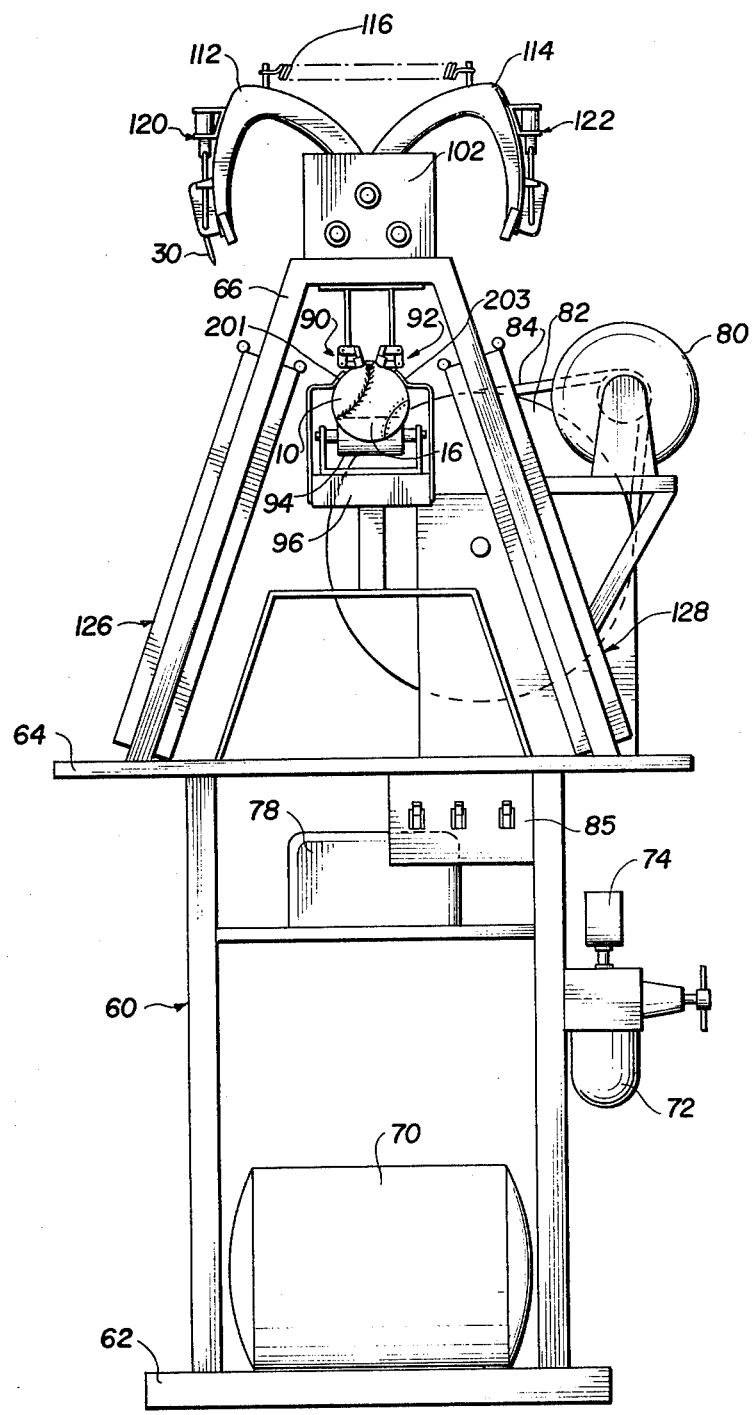
Figure 10:
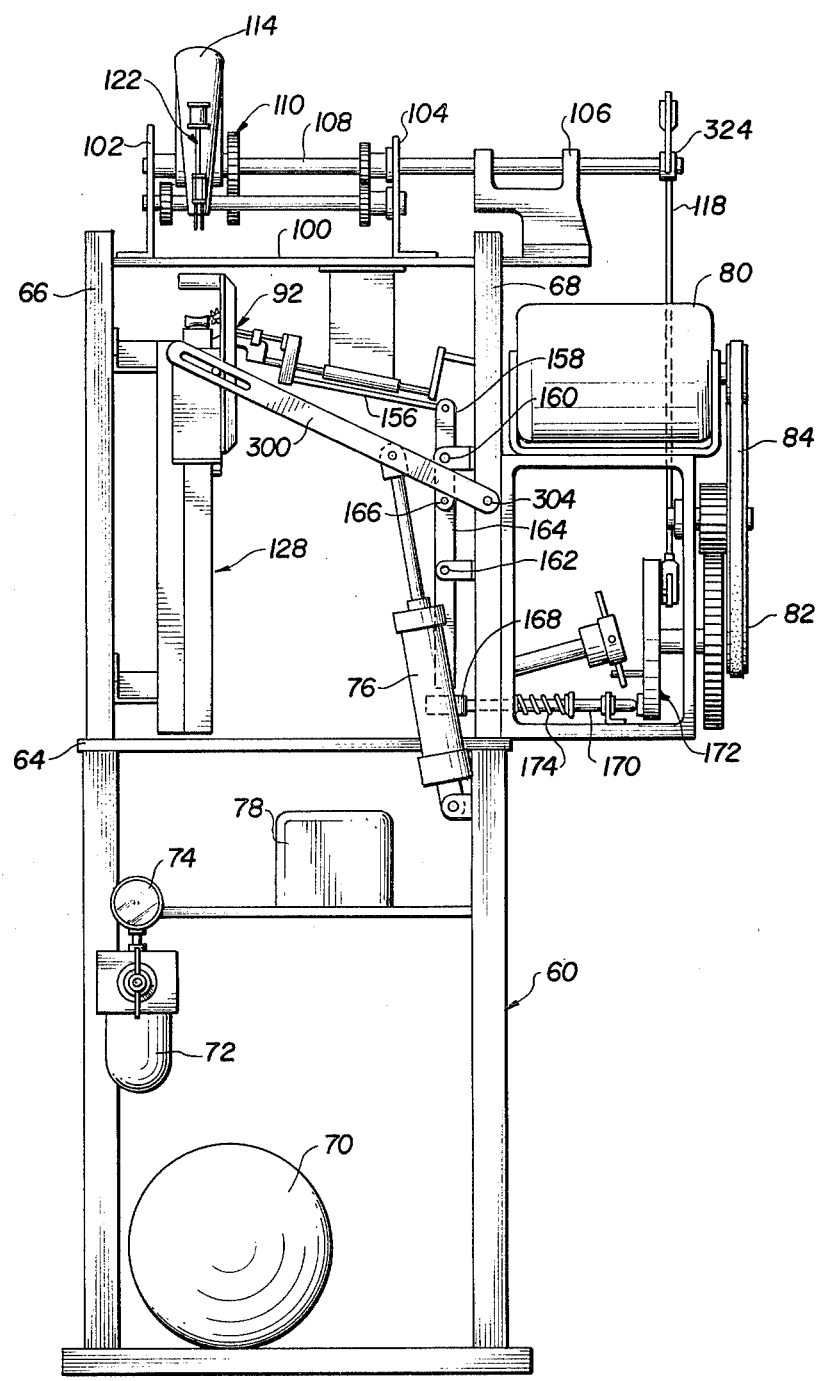
Figure 23:
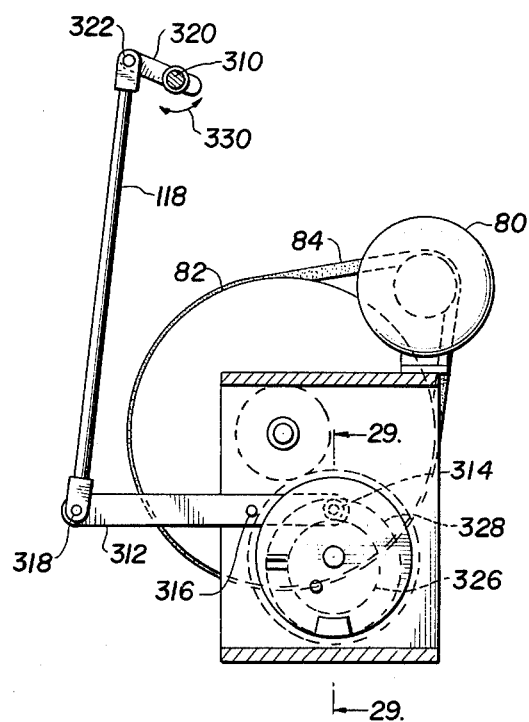
Figure 24:
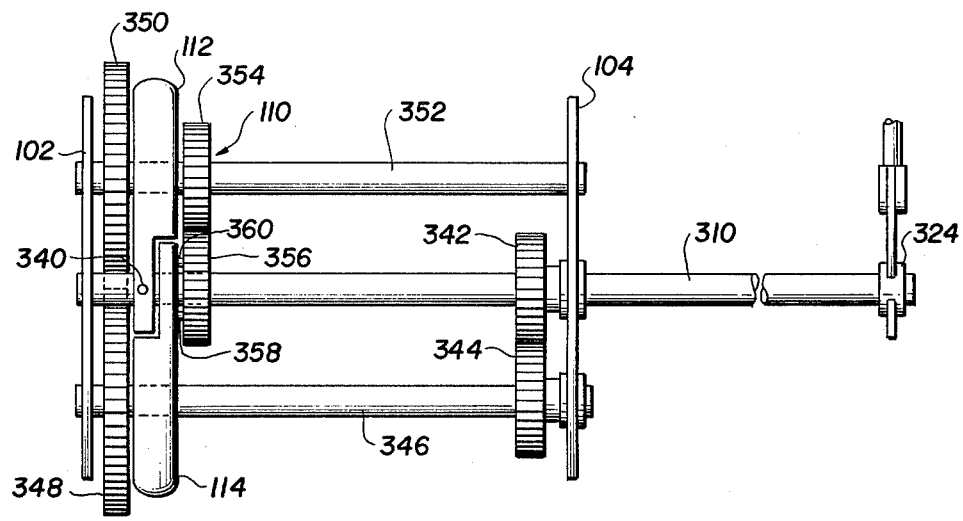
Figure 25:
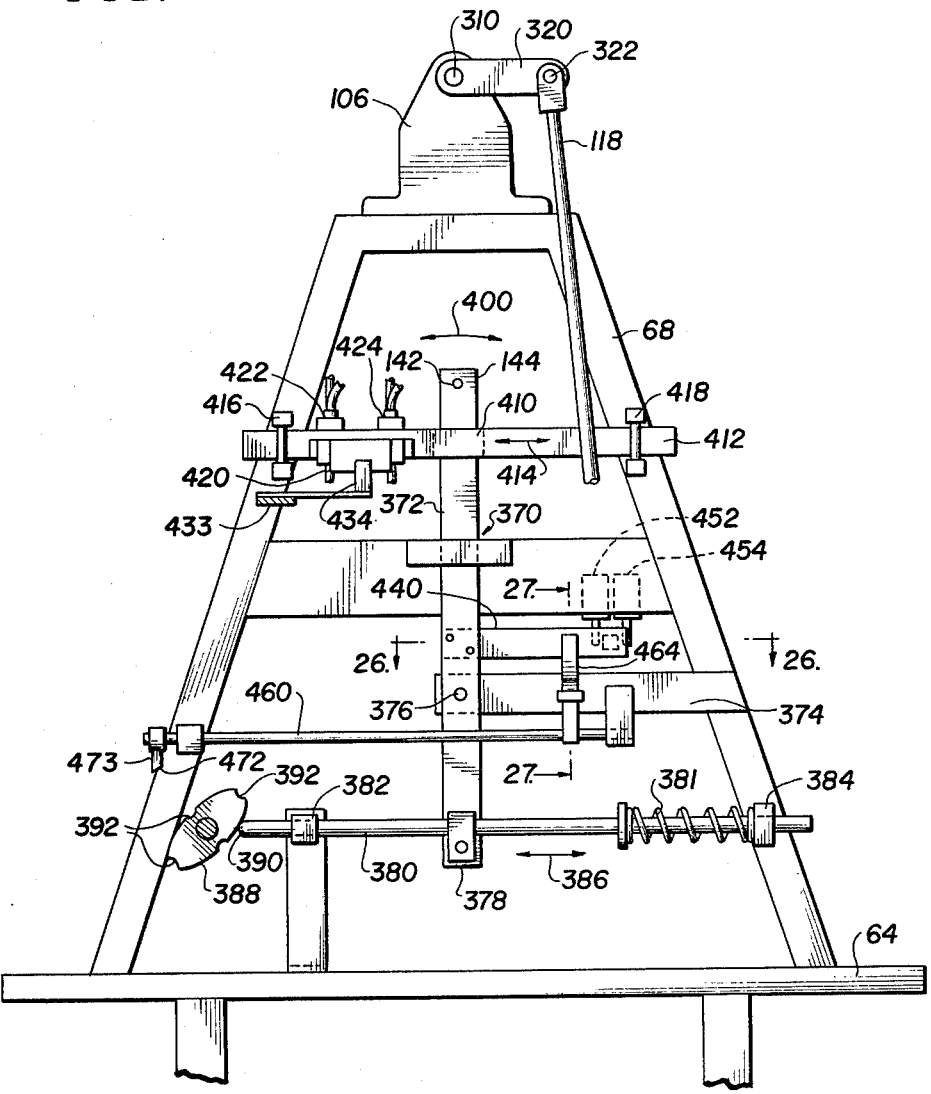
Figure 28:
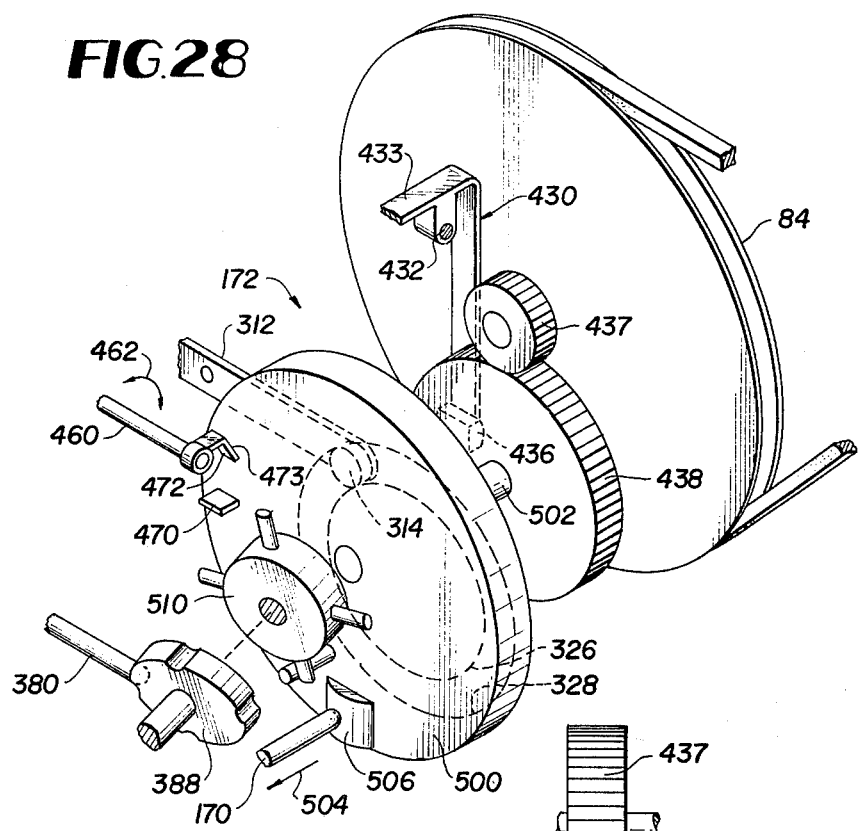
Figure 29:
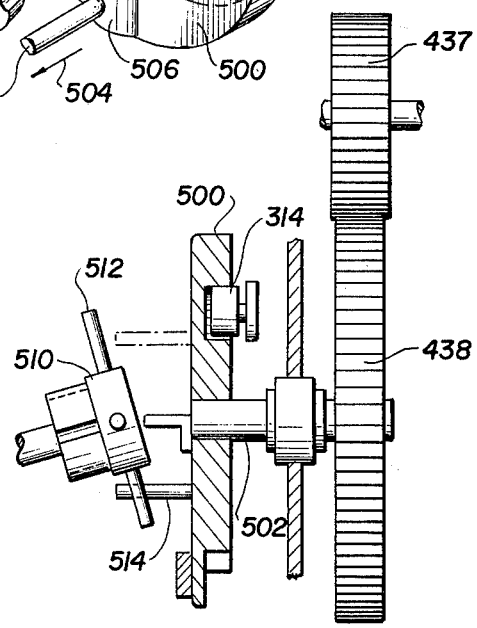

FIGS. 7a-f depict a schematic sequence of views whereby a pair of needles serves to stitch a baseball herringbone pattern between cover halves of a ball in accordance with a preferred embodiment of the invention;

FIG. 8 is a detailed plan view of a segment of a baseball cover stitched in accordance with the sequence illustrated in FIGS. 7a-e and in accordance with the invention;

FIG. 9 is a front elevational view of the subject apparatus showing a skeletal arrangement of the machine parts wherein numerous components have been eliminated for clarity of illustration;

FIG. 10 is a side elevational view of the subject apparatus depicted in FIG. 9;

FIG. 11 is a side elevational view of a ball handling assembly in accordance with the invention;

FIG. 12 is a side elevational view of the member depicted in FIG. 11 in an alternate mode;

FIG. 13 is a front view of the ball handling assembly depicted in FIG. 11 and discloses the edges of cover halves fitted between cover handling lobes and advancing sprockets;

FIG. 14 is a partial detail view of the assembly depicted in FIG. 13 wherein an edge of a cover half adjacent an advancing needle is positioned in a reclined posture while the edge of an opposing cover half is elevated to receive the tip of the advancing needles through apertures within the cover half;

FIG. 15 is a partial side view of a cover biasing strip as disclosed in FIG. 14;

FIG. 16 is a bottom view of the mechanism depicted in FIGS. 13 and 14 and particularly discloses a thread positioning and lifting tab used to create a herringbone stitch pattern during a sewing operation;

FIG. 17 is a detailed side elevational view of a double throw solenoid actuating mechanism used to lock onto the ends of stitching needles;

FIG. 18 is a partial detail view of the double throw mechanism depicted in FIG. 17 in an opposite or release posture;

FIG. 19 is a cross-sectional detail view taken along section 19—19 in FIG. 17 and discloses pin like tip members which serve to lock into receiving apertures within the ends of the stitching needles;

FIG. 20 is a partial axonometric view of a thread receiving and tensioning mechanism in accordance with the invention;

FIG. 21 is a partial axonometric view of the tensioning mechanism depicted in FIG. 20 in a lowered or tensioned posture;

FIG. 22, note sheet 10, is a partial detail view of the thread receiving mechanism showing the manner in which bristle tips operate to retain threads received within frame members;

FIG. 23, note sheet 11, is a partial detail view disclosing a double cam and lever mechanism utilized to operate needle pushing and pulling or shuttle arms as depicted in FIG. 9;

FIG. 24 is a plan view of a gear train actuated by the mechanism depicted in FIG. 23 for simultaneously raising and lowering needle handling or shuttle arms as depicted in FIG. 9;

FIG. 25 is an elevational view of a cam operated assembly operable for rocking the ball handling assemblies depicted in FIGS. 11 and 12, for positioning solenoid switches to operate the needle catching mechanisms depicted in FIGS. 17-19, and for positioning pneumatic switch contacts to operate the thread tensioning members depicted in FIGS. 20-22;

FIG. 26, note sheet 10, is a partial detail view of an electrical switch mechanism to actuate the needle catching mechanisms depicted in FIGS. 17-19;

FIG. 27 is a side elevational view of the electrical contact mechanism depicted in FIG. 26;

FIG. 28, note sheet 13, is a partially exploded axonometric view of a cam actuating and synchronizing assembly for (1) advancing the ball cover halves, (2) positioning the solenoid and pneumatic switches and rocking the ball handling mechanism, (3) actuating the solenoid switches, (4) operating the needle carrying shuttle arms, and (5) operating the pneumatic switches leading to the thread tensioning assemblies;

FIG. 29 is a partial side elevational view of mechanism depicted in FIG. 28; and FIGS. 30a-d disclose a schematic sequence of needle and thread handling in accordance with a preferred embodiment of the invention.

DETAILED DESCRIPTION

Figure 1:
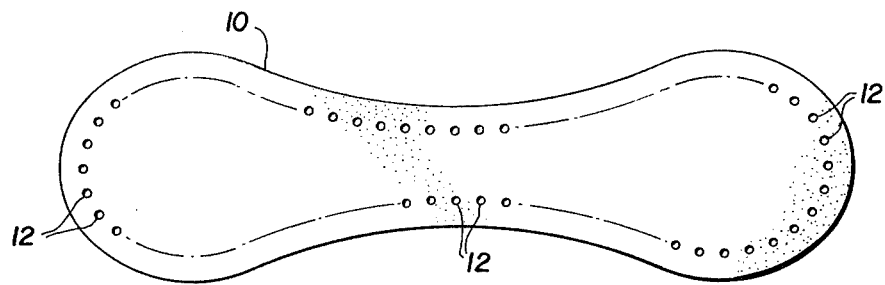
FIG. 1 is a plan view of a baseball cover piece or half to be sewn about a ball core.

Referring now to the drawings and particularly to FIG. 1 thereof, there will be seen a ball cover half 10 comprised of horsehide or the like, fashioned in a general elliptic lemniscate configuration wherein a plurality of thread receiving apertures 12 have been prepunched around the periphery of the cover.

Figure 2:
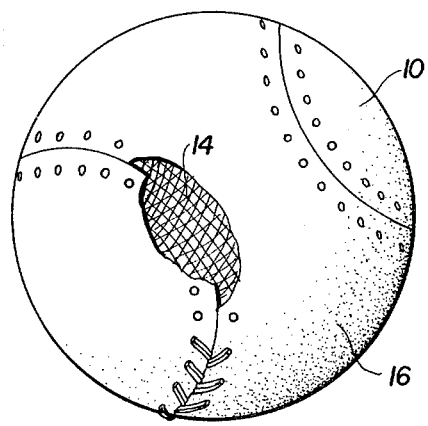
FIG. 2 is a perspective view of a pair of baseball cover halves of the type shown in FIG. 1 assembled about a baseball core with the start of a conventional double herringbone stitch pattern used to sew the cover halves together.

FIG. 2 discloses an axonometric view of a conventional baseball having a core or foundation portion 14 which is fashioned from a spherical inner member wrapped by a continuous elastic strand to a high degree of spherical tolerance and weight. The cover piece 10 along with an identical cover piece or half 16 is then wrapped around the core 14 to form a conventional baseball cover. The cover pieces 10 and 16 are preferably preformed by steaming or the like so they will mate with the exterior surface of the core 14. A slight amount of elastic adhesive is placed on the inner surface of the cover halves 10 and 16 so that the covers may be temporarily secured to the core 14 prior to a sewing operation.

Figure 5:
FIG. 5 is a cross-sectional view taken along section line 5—5 in FIG. 4 and discloses a thread receiving aperture positioned intermediate the ends of the stitching needle.
Figure 6:
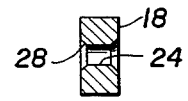
FIG. 6 is a cross-sectional view taken along section line 6—6 in FIG. 4 and discloses an aperture which is operably used by the subject apparatus to receive a transverse pin to push the needle in one direction and catch and pull the needle in an opposite direction during a sewing operation.
Figure 3:
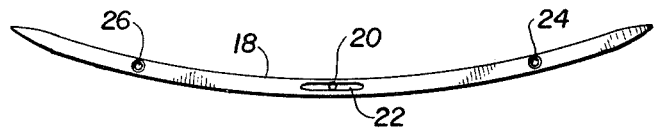
FIG. 3 is a side elevational view of a stitching needle used to sew cover halves to a core in accordance with a preferred embodiment of the invention.
Figure 4:
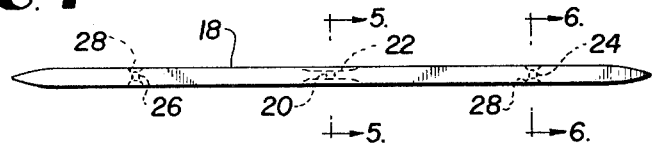
FIG. 4 is a top view of the needle depicted in FIG. 3.

Turning now to FIGS. 3-6 there will be seen various views of a needle 18 operable for use with the subject invention. More specifically, the needle 18 is gently arcuate in side elevational view, note specifically FIG. 3, and is fashioned with a transverse aperture 20 positioned approximately at a point intermediate the ends of the needle. As depicted in FIG. 5 it will be seen that the aperture 20 has chamfered surfaces 22 to readily receive the free end of a baseball stitching thread during a threading operation and to facilitate passage of the needle carrying a thread through a cover aperture. Each end of the needle 18 is provided with a transverse aperture 24 and 26 which is also provided with chamfered outer surfaces 28 so as to readily receive retaining pins from a solenoid actuated locking mechanism as will be discussed in detail hereinafter.

Referring now to FIGS. 7a-f there will be seen a sequence of views wherein the results of a conventional, alternate hand, back and forth sewing operation for a baseball cover are achieved by the subject mechanized invention to provide an over/under herringbone pattern as required by the softball and baseball industries. More specifically, FIG. 7a discloses first 30 and second 32 needles wherein a first thread 34 and a second thread 36 have been looped through central apertures in the needles as previously discussed. The needles initially are in a posture adjacent cover halves 10 and 16 overlaying a ball core or foundation 14. As depicted in FIG. 7a the first and second needles pass over an edge of the cover half 16 and under and through apertures 38 and 40 of the edge of the opposing cover half 10. Maintaining the adjacent edge of the ball cover half in a reclined position and the opposing edge in an upward posture as the needles 30 and 32 advance during the stitching operation is performed by ball handling assemblies which will be described in detail with specific reference to FIGS. 13-15.

Turning to FIG. 7b, there is a further schematic representation of a next sequential operation in the stitching process wherein the needles 30 and 32 have been pulled completely through the cover apertures 38 and 40 and have drawn first and second threads 34 and 36 respectively through the edge of cover half 10. Tensioning and string handling bars 42 are schematically depicted in FIG. 7b and will be discussed more fully with relation to FIGS. 19-21; functionally, however, the bars 42 serve to engage the first and second threads and pull the threads into secure and tight engagement with the underlying surface of the ball cover 10.

Turning now to FIG. 7c, the needles are retained in the same transversely parallel planes while the ball cover halves are rotated or advanced by a mechanism such as depicted in FIGS. 11 and 12 whereby apertures 44 and 46 lie within the same vertical plane as apertures 38 and 40 previously occupied. In this posture the first and second needles 30 and 32 are reversed in direction and pushed over the adjacent edge of cover half 10 and under and through the opposing edge of cover half 16.

Looking now at FIG. 7d the first and second needles 30 and 32 have been caught by a shuttle arm and pulled completely through the apertures 44 and 46. Another set of tensioning and string handling bars 48 are then actuated which serves to pull the first and second threads 34 and 36 through the apertures 44 and 46 and draw the edgemost portion of the cover 10 into close proximity to the opposing abutting edge of cover half 16.

FIG. 7e depicts the next sequential event wherein the ball cover halves 10 and 16 are advanced or indexed another position such that apertures 50 and 52 in the edge of cover half 10 are in the plane of reciprocating needles 30 and 32 which had previously been occupied by apertures 44 and 46. Prior to advancing of the needles, the edge of cover half 16 adjacent the tips of the advancing needles is laid down while the edge of the opposing cover half 10 is elevated such that the needles will pass over the edge of cover 16 and under and through the edge of cover 10 in a manner previously outlined in connection with FIG. 7a. In this subsequent stitching operation, however, a lifting mechanism 54, note also FIG. 15, engages the second thread 36 and lifts it to a posture intermediate the spacing of advancing needles 30 and 32 and above the path of advancement of needle 30 such that the first thread 34 is laid beneath the second thread 36 as it advances through the aperture 50.

FIG. 7f depicts the position of the needles following a full cycle wherein the needles 30 and 32 have been caught and pulled completely through apertures 50 and 52 and the full length of the first and second double threads has been pulled through the apertures by the tensioning bars 42. This tensioning pulls the edge portion of cover 16, intermediate the apertures 44 and 46, into a close abutting position with respect to the opposing surface of cover half 10.

The above process is repeated at a rapid rate about the seam of the cover halves to form, upon completion, a uniform, tight, double thread, herringbone seam such as depicted in FIG. 8 and as required by the industry.

The previously discussed stitching operation is automatically terminated upon completion of essentially the entire ball seam and return of the needles to within one or two stitches of aperture 38. At this point in time the ball is removed from the mechanical stitching assembly and the final two or three stitches are completed by hand and tied in a conventional manner.

FIGS. 9 and 10 disclose an apparatus for performing the previously discussed baseball stitching sequence in accordance with a preferred embodiment of the invention. In this connection the apparatus includes a frame 60 having a base 62 and an elevated platform 64. Mounted upon the platform 64 is a forward and rearward A-frame assembly 66 and 68 respectively for mounting the various operating assemblies of the subject invention. An air cylinder 70 is fed by a conventional source of air pressure and is mounted upon the base. The air cylinder serves to store air pressure which is fed through an accumulator 72 and pressure gauge 74 to thread tensioning cylinders 76 which are mounted upon opposite sides of the unit. The apparatus is further provided with an AC to DC transformer 78 which supplies current for operating needle catching assemblies to be discussed more fully with respect to FIGS. 16-18. The apparatus is further powered by a conventional AC electric motor 80 mounted upon the rear A-frame 68. The motor is drivingly coupled to a reducing flywheel 82 by a flexible connector or drive belt 84. On/off control for the various air pressure drive motor and transformer functions may be controlled by a conventional switch panel 85 mounted upon the A-frame.

A baseball or the like to be machine sewn by the subject apparatus is carried by a pair of ball handling and mounting heads 90 and 92 which engage cover halves 10 and 16 as depicted in FIG. 9. The ball is further supported against rearward translation by a roller 94 which is mounted upon a support bracket 96 carried by the platform 64. (The rear roller 94 and supporting bracket are not depicted in FIG. 10 in order to clarify other structural features of the invention).

A generally horizontal structured plate 100, note FIG. 10, extends between the uppermost portion of A-frames 66 and 68 and serves to carry end brackets 102 and 104 and a bearing assembly 106 operable to support a central shaft 108 of a gear train 110. As will be discussed more fully in connection with FIGS. 22 and 23 the gear train serves to operate first and second needle carrying shuttle arms 112 and 114 respectively. The shuttle arms 112 and 114 are biased in an upward posture by the provision of a spring 116 as depicted in FIG. 9 but are principally raised and lowered through rotation of shaft 108 and drive train 110 from actuation of a rod assembly 118, note FIG. 10. This rod assembly is driven by a double cam mechanism which will be discussed in detail with respect to FIGS. 22-28.

Returning to FIG. 9 the shuttle arms 112 and 114 carry solenoid actuated gripping assemblies 120 and 122 which serve to engage and retain opposite ends of the needles 30 and 32 as schematically discussed above and as will be discussed in detail with respect to FIGS. 16, 17, and 29a–d.

At a forward end of the apparatus, and in a posture adjacent to A-frame 66, a first 126 and second 128 tensioning and thread handling assembly are mounted substantially within a vertical plane of movement of the shuttle arms 112 and 114. These assemblies will be discussed further with respect to FIGS. 19, 20, and 21, but are normally held in an upper posture and out of engagement with the threads as depicted in FIG. 10. Actuation of the tensioning and thread handling assemblies in a rapid down/up reciprocating mode is provided by air cylinders 76, note FIG. 10, on each side of the apparatus.

Referring now to FIGS. 11 and 12 there will be seen a ball handling assembly 92 as previously noted in connection with FIGS. 9 and 10.

The ball handling assembly is supported from the structural plate 100 which serves to carry a downwardly extending brace 130. A cylindrical bearing 132 is carried by the remote end of the brace and serves to receive a solid cylindrical rod 134 which is held against translation within the bearing 132 by collars 136 and 138. A rearward end of the rod 134 is fixedly connected to a yoke 140 and a base portion of the yoke is connected to a rod 142 connected to an actuating bar 144. The actuating bar is operable to be translated in a generally horizontal mode back and forth with respect to the stationary brace 130 and serves to rotate rod 134 as will be discussed more fully below.

The other end of the rod 134 is fixedly connected to and carries a guide member 146 which in turn carries a needle and thread guide 148 and a cantilever lip 150 operable to be received beneath an adjacent edge of a cover half to be sewn upon a ball. A yoke 152 is slidably carried at the forward end of the rod 134 and has a central enlargement at the base thereof to fixedly receive another rod 154 which is substantially parallel with rod 134.

Rod 154 may be translated as indicated by directional arrows 156 in a back and forth mode by the provision of a downwardly extending arm 158 of a dual pivot linkage, note FIG. 10. More specifically, the dual linkage includes a first pivot 160 and a second pivot 162 which serves to carry link 158 and a corresponding arm 164. The members 158 and 164 are pivoted together at 166. The lowermost end of arm 164 is connected via a ball joint 168 to a generally horizontally extending shaft 170. The shaft 170 is operated in a forward direction by a cam assembly 172, which will be discussed more fully in connection with FIGS. 27 and 28, and in a return direction by compression spring 174. As can be appreciated in FIG. 10, translation of the rod 170 in a right to left direction will serve to correspondingly translate shaft 156 from right to left, as viewed in FIG. 10, which in turn, will carry the yoke 152 forward upon the rod 134.

A bracket 173, note FIG. 11, is connected to one arm of the yoke and in turn serves as a mounting for a rod 175 extending through a bearing 176. The rod 175 is connected to a three part linkage system having a first link 177, a second link 178 and a third link 179 mounted upon the ball handling assembly 92. The rod 175 and link 177 are held in a generally fixed planar position by a releasable pin 182. The second link 178 is pivotably mounted upon member 146 and pivotably carries a paw 184 which is spring biased by a spring 186 into engagement with a ball advancing sprocket 190. The advancing sprocket is pivotably mounted upon a free end of the third link 179 and is free to rotate in response to a driving action of the paw 184.

In the above connection and with specific reference to FIG. 12 it will be seen that the shaft 154 has been retracted carrying the yoke 152 rearwardly until it engages a stop 188. This action in turn draws rod 175 through the bushing 176 and the second linkage 178 pivots counterclockwise to drive the paw 184 and sprocket 190 in a counterclockwise motion as well. During this movement the peripheral projections or teeth 192 of the sprocket, which are operatively engaged with apertures in a cover half, are rotated one notch such that a cover half engaged with the ball handling mechanism will be advanced a distance equal to the spacing between adjacent apertures relative to the needle guide 148. In order to permit the rotation of the second link 178 with respect to the stationary member 176, the linkage connection at 194 is provided with a slightly slotted aperture in the second link.

Upon return of the indexing rod 154 in the opposite direction, and contact of a stop 196 against the bushing 176 the paw will be permitted to drag over the top of the next sprocket tooth 200 and is reset by the spring 186.

Referring now to FIGS. 13–16 the ball-handling assembly 92, as depicted in FIGS. 11 and 12, is shown in an installed posture adjacent to and identical with a mirror image ball handling assembly 90. During operation the ball core 14 and cover halves 10 and 16 are mounted between the cantilever lips 150 and 150' and needle guides 148 and 148' and drive sprockets 190 and 190'. More specifically during the ball mounting operation the locking pin 182 of each ball handling apparatus, note FIG. 11, is removed and the first, second and third linkages are pivoted upward and adjacent ball cover edges are inserted over the cantilever carrying lips 150 and 150' in a posture depicted in FIG. 13. At the same time biasing arms 201 and 203, note FIGS. 14 and 15 are applied on top of the cover halves 10 and 16 respectively to assist in holding the leather halves and to facilitate flexing of the edges thereof during stitching. Following this mounting operation, the linkages 177, 178 and 179 are pivoted downwardly and two of the projections 192 of each of the drive sprockets are engaged with adjacent apertures in respective edges of the cover halves.

Turning to FIG. 14 it will be seen that during operation of the stitching assembly, the bar 144, note FIG. 11, translates the base of the yoke 140 which serves to rotate rods 134 and 134'. This action lifts the edge of cover half 16 and depresses the edge of cover half 10 with respect to a neutral mounting posture such as depicted in FIG. 13. In this position with the edge of cover 10 lowered and the edge of cover 16 raised, the needles may operatively advance in a gentle arc as indicated by directional arrow 191 over the edge of cover half 10 and through apertures provided in the edge of cover half 16. The provision of biasing member 203 particularly facilitates controlled raising of the cover edge as depicted in FIG. 14.

The position of the cover edges shown in FIG. 14 may be reversed by reversing the transverse motion of the sliding bar 144 in a manner which will be discussed in detail in connection with FIG. 24.

FIG. 16 is a bottom view of the ball handling assemblies 90 and 92 and specifically discloses the needle guides 148 and 148' which are each fashioned with arcuate cutout portions 210 and 212 for receiving and guiding the needle tips through the ball cover halves. Additionally FIG. 15 specifically discloses a tab projection 54 which serves to position and lift a second thread relative to advancing needle tips in a manner as previously discussed in connection with FIG. 7e.

Referring now to FIGS. 16–18 there will be seen a solenoid operated needle catching assembly 122 such as previously depicted in FIGS. 9 and 10. More specifically a pair of reversely acting solenoids 220 and 222 surround a central drive shaft 224 which is pivotally connected at 226 to a three link over the center locking mechanism 228. In this regard a first link 230 is pivotably connected to a second link 232 at 226 and the first and second links are pivotally connected at 234 and 236 to a stationary backing member. The free ends of links 230 and 232 are biased together by the provision of a tension spring 240. By the provision of the foregoing over-the-center mechanism, operation of the shaft 224 in either direction will serve to set the linkage mechanism 228 in either a first position depicted in FIG. 16 or a second position as depicted in FIG. 17.

A further shaft 242 is connected to the pivot 226 and engages a guide extension 243 and first 244 and second 246 linkage arms. The first and second arms connect to parallel arms 248 and 250 which are pivoted at 252 and 254 respectively and carry at the remote free ends thereof connecting pins 256 and 258. The connecting pins 256 and 258 are guided by bushings 260 and 262 which serve to guide tips 264 and 266 of the pins into apertures at the ends of needles 30 and 32.

Each of the shuttle arms 112 and 114 is provided with a solenoid actuated catching mechanism as described above to selectively catch and release the needles 30 and 32.

Referring now to FIGS. 19 and 20 there will be seen detailed axonometric views of a thread handling and tensioning mechanism 128 as previously discussed in connection with FIGS. 9 and 10. More specifically each of the tensioning and thread handling assemblies includes a generally U-shaped frame 270 having one or more channels such as channels 272 and 274 within the interior of the frame. The internal wall surfaces of the channels 272 and 274 are lined with mutually opposing bristles 276, 278, 280, and 282 respectively. A translating housing 284 is fitted about the frame 270 and carries first 286 and second 288 thread engaging pins. These thread engaging pins were previously schematically depicted in FIG. 7d as blocks 48. In a preferred embodiment, however, the cross-sectional configuration of the thread engaging members are preferably somewhat tear shaped in design, note particularly FIGS. 20 and 21, and operably engage the first and second threads extending across bearing pads 290, 292 and 294 for driving the threads downwardly into the opposing bristle combinations during a thread tensioning sequence.

The driving action for the thread engaging members 286 and 288 is provided by pneumatic actuation of the parallel arms 300 and 302 which are pivotably mounted to the A-frame 68, note FIG. 10 at a pivot point 304. The arms are pulled downwardly and then driven upwardly through actuation of a double acting air cylinder 76. An identical air cylinder is mounted upon the opposite side of A-frame 68 to actuate the assembly 126.

As the translating frame 284, carrying the thread engaging bars 286 and 288, is raised the tear shaped configuration of the bars facilitates reverse movement through the opposing brush pads while leaving the threads in a stored sinuous posture within the tips of the brush ends, note FIG. 21.

The threads are maintained within the thread handling chambers 126 and 128 mounted upon either side of the A-frame 66, note FIG. 9, until the needles 30 and 32 have advanced to the other side of the apparatus and the alternate pair of thread tensioning pins descend within the alternate thread handling member 126 to pull the threads up through the bristle retaining members in assembly 128, through the ball cover and down into the opposing thread handling assembly 126.

Referring now to FIG. 21 there will be seen a detail cross-sectional view of the thread handling mechanism 270 wherein the tensioning members or bars 286 and 288 are shown in a posture pulling the threads downwardly through the tips of the brushes 276, 278, 280 and 282. It will be seen that in this posture the tips of the opposing brush segments are operable to engage with and retain the first and second threads within the elongate chambers 272 and 274.

FIG. 22 discloses a cam and mechanical linkage assembly operable to raise and lower rod assembly 118 and pivotally drive shaft 310. More specifically a first lever arm 312 is fitted at one end with a cam follower 314 and is pivoted about a point 316. The other end of the arm 312 is pivotally connected to one end of the lifting rod 118 at 318. The other end of rod 118 is pivotably connected to a linkage 320 at 322. The linkage 320 in turn is fixedly connected to the shaft 310 by a collar 324, note FIGS. 10 and 23.

The cam follower 314 rides on the surface of a cam 326, note FIGS. 22 and 27. Accordingly as the cam 326 is rotated in a clockwise direction, as viewed in the direction of FIG. 22, the follower will raise thus lowering pivot points 318 and 322 and rotating shaft 310 in a counterclockwise direction. As the cam 326 passes its maximum offset dimension, an outer cam surface 328 engages the upper portion of the follower 314 and pulls or forces the end of the linkage 312 downwardly thus raising pivot point 318 and 322 and rotating shaft 310 in a clockwise direction as indicated by directional arrows 330.

Turning now to FIG. 23 there will be seen a plan detail view of a mechanical gear train operating off of shaft 310 to raise and lower shuttle arms 112 and 114 in pivotal unison. More specifically, shaft 310 is directly connected to needle carrying shuttle arm 112 by a conventional fastener such as a set screw or the like 340. Accordingly, as the shaft 310 rotates in a clockwise direction, the arm 312 will be similarly rotated and when the shaft 310 is rotated in a counterclockwise direction the shuttle arm 112 will follow.

Three sets of spur gears comprise the gear train 110 which is driven by the shaft 310 to effect simultaneoous but opposite driving of shuttle arm 114 with respect to arm 112. In this regard first gear 342 is connected to shaft 310 and serves to drive gear 344 which in turn is mounted upon shaft 346. The shaft 346 carries gear 348 which meshes with a similar gear 350 mounted upon shaft 352. Shaft 352 carries gear 354 which directly meshes with spur gear 356 which in turn is connected via pins 358 and 360 to the shuttle arm 114. By the provision of the gear train 110 rotation of the shaft 310 in a clockwise direction will effect an opposite or counterclockwise rotation of shuttle arm 114.

The practical effect of the foregoing is to provide a mechanical gear assembly 110 operable to simultaneously raise and lower shuttle arms 112 and 114 in synchronized unison toward and away from the ball to be stitched. Accordingly, and as will be discussed in detail with respect to FIGS. 29a-d, the shuttle arms 112 and 114, in cooperation with solenoid locking mechanisms 120 and 122, are operable to push and pull the needles 30 and 32 through the ball cover halves and exchange the needles from one arm to the other during the process.

Referring now to FIG. 24 there will be seen a schematic representation of the back of the subject apparatus wherein the various control functions are mechanically synchronized. More specifically, the A-frame 68, also note FIG. 10, carries at its uppermost portion bearings 106 for the previously discussed shuttle driving rod 310. This shaft is driven by the linkage mechanism 318 and 320 as previously discussed.

Located beneath the bearings 106 the A-frame 68 carries a positioning and drive apparatus to rock the ball handling assemblies 90 and 92, and a switch positioning assembly 370. More specifically, a bar 372 is pivotally mounted upon a generally horizontal extending support 374 at 376. The lower end 378 of the bar 372 is connected to a generally horizontal shaft 380 which is journaled at its ends at 382 and 384 for longitudinal reciprocation as indicated by directional arrows 386. This reciprocation is provided by rotation of a cam 388 which bears against one end 390 of the shaft 380 and a return spring 381.

The cam 388 is designed to dwell at 90° rotational intervals and is provided with a plurality of arcuate surfaces 392 for intimate engagement with a compatable surface at the end of shaft 380. The shaft 380 is maintained in a contact posture with respect to the cam 388 by the compression spring 381. Rotation of the cam 388 will accordingly serve to reciprocate the shaft 380 along the line of directional arrows 386 and correspondingly pivot the upper end 144 of the bar 372 back and forth generally as indicated by directional arrows 400. The upper end of bar 372, as previously discussed in connection with FIG. 11, serves to carry rod 142 in a back and forth mode and thus rock the ball handling assemblies 90 and 92 to alternately raise and lower the edges of cover halves 10 and 16 during a stitching operation.

Sychronization of the cover manipulation operation, as initiated by cam 388, is insured in a manner which will be discussed more fully in connection with FIG. 27.

In addition to rocking the ball handling assemblies 90 and 92 the assembly 370 serves to position solenoid and pneumatic switches which operate the needle grasping and thread tensioning and handling mechanisms respectively.

More specifically and returning to FIG. 24, the upper portion of the bar 372 extends through bracket 410 mounted upon a generally horizontally extending bar 412 which in turn is mounted for reciprocation along the line of directional arrows 414 by end receiving assemblies 416 and 418. Reciprocation of rod 412 serves to position a pivotally mounted contact plate 420, connected to rod 412, in alignment with either a first 422 or second 424 parallel/crossing pneumatic valve. These pneumatic valves are fed from the air compressor cylinder 70 via the accumulator 72. Output from the parallel and crossing valves 422 and 424 is fed directly to the opposite ends of the thread handling air cylinder 76 on the right hand side of the machine as viewed in FIG. 9 and a similar such air cylinder mounted upon the left hand side of the machine, not shown. The air cylinders actuate the thread tensioning mechanisms 126 and to 128 as specifically discussed in connection with FIGS. 10, 19, 20 and 21.

Actuation of either the first or second air valves 422 or 424 is achieved by a linkage assembly 430, note FIG. 27. In this regard a pivot axis 432 carries an actuating arm 433 which is connected to an actuating paw 434, note FIG. 24, which rests against the pivotally mounted plate 420. Actuation of the linkage mechanism 430 is achieved by a cam surface 435 which rides upon the outside of the spur gear 438, note FIG. 27. The contact plate 420 is biased away from valves 422 and 424 so that actuation of either valve is relatively momentary as the spur gear rotates the cam 438 past the end of linkage assembly 430. At this point the pivot plate 420 will be pivoted into contact with one of the air valves as selected by the position of bar 412 and will thus reverse the direction of air flow to the pneumatic cylinders for a moment to drive the thread tensioning bars downwardly and then bring the bars back to their elevated position. This actuation has the effect of pneumatically driving the thread handling members 286 and 288 rapidly downwardly through the brush tips to draw the thread through the ball cover and tension the thread within the handling chambers 270. Following this downward tensioning sequence, which may be regulated by the air pressure maintained within the chamber 70 and accumulator 72, the thread contact arms 286 and 288 are rapidly repositioned in a normal upper position by repositioning of the air valves.

In addition to controlling the position of the contact for the air valves, the assembly 370 positions the contact for solenoid valves.

Referring to FIGS. 24-26 a resilient bar 440 is mounted upon the bar 372. Actuation of the rod 380 will serve to translate the bar 440 along the path of directional arrows 442 and 444 to bring a contact land 446 into an opposing posture with respect to a contact roller 448 or 450, note FIG. 25, connected to electrical contacts 452 and 454 respectively, note FIG. 24.

Once the contact land 446 is positioned in a posture opposing a contact roller 448 or 450, actuation of the electrical switch may be achieved by pivoting action of a rod 460 as indicated by directional arrows 462 in FIGS. 26 and 27. Such actuation or rotation of arm 460 will serve to rotate contact arm 464 which bears against bar 440. Actuation of either electrical contact switch 452 or 454 is achieved at a synchronized moment in time by contact of a narrow land 470, note FIG. 27, carried by wheel 500 upon a lowermost sloping surface 472 of a tab 473, note FIG. 24. The shaft 460 is biased into a ready position by the provision of a spring assembly such as spring 474, note FIG. 26, which biases the contact arm 464 against an abutment 476. In addition outward bias is provided by the resiliency of bar 440 which is fashioned with transverse V slots 476 and 480.

Electrically the transformer 78 is connected through the switches 452 and 454 to the double solenoids 420 and 422 of each of the needle catching mechanisms 120 and 122. The lines, however, between each catching assembly 120 and 122 are reversed such that when one of the contact switches 452 and 454 is actuated the solenoid releasing assembly 120 will be operated in one direction to either catch or release the needles while the opposing assembly 122 is actuated in a reverse direction to perform the reverse operation. By this technique the needles may be passed back and forth between the shuttle arms 112 and 114 as previously mentioned.

The previously discussed motions of advancing the ball cover halves, raising and lowering the edges of the ball cover halves, actuating the needles 30 and 32 from side to side in a shuttle mode over and through the ball cover halves, releasing and catching the ends of the needles to push and pull the needles through the ball cover halves and actuation of the pneumatic thread tensioning and handling assemblies are all synchronized in order to permit a rapid, smooth and continuous stitching operation. In a presently preferred embodiment all of these functions are initiated from a cam center 172 as previously noted in connection with FIG. 10.

Referring now to FIGS. 27 and 28, the central cam wheel 500 is driven by the fly wheel 84 via a spur gear combination 437 and 438. In this connection a shaft 502 directly interconnects the center of gear 438 with the cam wheel 500 through a stationary housing wall 503 connected to the frame. The axonometric view shown in FIG. 27 is exploded so as to facilitate illustration of the relationship of the various members which in operation will be fitted together in a manner similar to that depicted in FIG. 28.

Considering then the various operating aspects of the subject apparatus, the ball advance or feeding operation is initiated by axial displacement of the shaft 170 in the direction of arrow 504. This motion occurs when the land 506 is brought into engagement with the end of the shaft 170, note FIGS. 10 and 27.

Rocking action of the ball handling units 90 and 92 is initiated by rotation of cam 388 which is driven by a hub 510, note FIG. 28, carrying four radially extending spokes 512. The hub 510 is canted with respect to the cam wheel 500 to an extent such that only one of the radial spokes 512 will be contacted by a normally projecting rod 514 during each full revolution of the wheel 500 (note the phantom representation of rod 514 in an upper position relative to the spokes 512). Accordingly, the hub 510 will be rotated 90° for every 360° of rotation of the wheel 500. This 90° rotation will serve to shift the rod 380 in one direction or permit its retraction in the other direction for each full revolution of the cam wheel 500. This shifting action, as previously discussed, performs the synergistic function of rocking the ball handling heads 90 and 92 and simultaneously positioning the contact for the solenoid switches and the pneumatic, thread handling, switches.

One down/up actuation of the shuttle arms 112 and 114, is achieved with each full revolution of the cam wheel 500 in that the cam follower 314 carried within the inner and outer cam surfaces upon the back side of the cam wheel 500 will raise and lower one time during each revolution of the wheel 500.

Additionally with each revolution of the cam wheel 500, the cam 436 riding upon the outside surface of the gear 438 will actuate one or the other of air valves 422 and 424 and one or the other of the solenoid contact switches 452 and 454 will be actuated by tab 470 contacting cam surface 472.

The foregoing discussion with respect to FIGS. 9 through 28 has been specifically directed to actuation of the various ball handling, thread handling and stitching motions through the provision of cam actuated and mechanically driven members. It will be appreciated by one skilled in the art who is familiar with the foregoing description, however, that other actuating systems may be utilized such as a plurality of air cylinders and/or solenoid devices or the like synchronized by a master control system.

Referring now to FIGS. 29a-d there will be seen a schematic representation of a general overall sequence of operation of the shuttle arms in accordance with a preferred embodiment of the invention. In this regard and with specific reference to FIG. 29, it will be seen that the apparatus is shown with a first stitch having been made with application of the thread tensioning and storing bars 42 to store the thread within the handling member 126. The needles 30 and 32, (not shown), have been pulled into an upper position by shuttle arm 112 and are ready to descend toward the ball cover. In this position the steps previously discussed in connection with FIGS. 7a and 7b have been performed.

FIG. 29b discloses the simultaneous descent of the shuttle arms 112 and 114 and delivery of the needle tips over cover half 10 and through the upwardly lifted edge of cover half 16 and into the catching assembly 122 of shuttle arm 114. At this point the solenoid switches are actuated and the left end of needles 30 and 32 are released from solenoid assembly 120 and the right end of the needles are caught by solenoid assembly 122.

Referring now to FIG. 29c, the internal cam 326 has functioned to simultaneously raise the shuttle arms 112 and 114 and pull the needles 30 and 32 through the edge of the ball cover. With the needles in an elevated out of the way posture, the cam 436 actuates the linkage mechanism 430 which actuates the parallel/crossing air valves to drive the thread contacting bars 48 downwardly against the threads. This rapid downward action serves to rapidly pull the thread away from the bristle tips of the storing chamber 126 through the ball cover and into the opposing storage chamber 128. At the same time, and most importantly, tension is applied to the stitch, note FIG. 29d. Due to the size of the cam 436 and the outward spring bias of the contact plate 420, actuation of the air cylinder in a downward mode is momentary and thus the thread contacting bars 48 will immediately return to the ready position between the shuttle arms 112 and 114.

The ball cover is indexed forward the distance between adjacent apertures and the ball handling assemblies 90 and 92 are rocked to the other side to lay down the edge of the cover half 16 and raise the edge of the cover half 10 for the return pass of the needles 30 and 32. On this return pass the tab 54 catches, raises and positions the second thread between the returning needles as previously discussed in connection with FIG. 7e to provide the herringbone stitch pattern as required by the baseball industry.

The foregoing operation is repeated and the shuttle arms move back and forth while the ball seam is indexed until the entire seam, with the exception of one or two stitches, is machine sewn. At this point the machine is automatically stopped via a stitch counter or motion limit mechanism (not shown) and an operator removes the ball so that the final two or three stitches and tying of the ball cover may be finished by hand.

SUMMARY OF MAJOR ADVANTAGES OF THE INVENTION

After reading and understanding the foregoing description of the invention, in conjunction with the drawings, it will be appreciated that several distinct advantages of the subject method and apparatus for mechanically stitching a baseball and the like are obtained.

Without attempting to set forth all of the desirable features of the instant invention, as specifically and inherently disclosed above, at least some of the major advantages include the concept of shuttling a pair of needles simultaneously back and forth across ball halves to be stitched while utilizing the tab 54 to form a herringbone stitching seam as required by the baseball industry.

The provision of the subject ball handling assemblies 90 and 92 facilitates accurate alignment and guiding of the shuttle needles as well as controlled and regulated advancement of the ball seams during a sewing operation.

Further the subject ball handling assemblies serve to raise and lower the edges of the cover halves so as to accurately receive the thread carrying needles without imparting mars, slits or foreign substances to the smooth exterior surface of the leather cover.

The subject ball indexing mechanism serves to positively position preformed apertures in the ball cover halves to accurately receive the tips of the shuttle needles.

Utilizing the foregoing machine, test estimates indicate that a single operator will be capable of simultaneously operating five machines and will be able to increase his production rate about 40 times over his present rate.

Additionally the subject thread tensioning and thread handling system provides a uniform tight seam between abutting edge surfaces of the cover halves and at the same time prevents the threads from becoming entangled during the rapid mechanical stitching operation.

Further the provision of a pair of needles, each carrying a dual thread, is capable of forming a dual thread herringbone construction required by the baseball industry wherein the V-shape of the seam lies directly upon the ball seam.

In describing the invention, reference has been made to a preferred embodiment and illustrative advantages of the invention. Those skilled in the art, however, and familiar with the instant disclosure of the subject invention may recognize additions, deletions, modifications, substitutions and/or other changes which will fall within the purview of the subject invention and claims.

What is claimed is:

1. A method for sewing cover halves together around a ball core comprising the steps of:
providing a first needle for carrying a first thread through an aperture transversely extending therethrough and intermediate the ends thereof;
providing a second needle for carrying a second thread through an aperture transversely extending therethrough and intermediate the ends thereof;
providing a ball core with first and second cover halves to be sewn together positioned around the ball core;
advancing the first and second needles in one direction over an edge of the first cover half and under and through an edge of the second cover half for carrying the first and second threads over the edge of the first cover half and under and through the edge of the second cover half;
advancing said first and second needles in an opposite direction over the edge of the second cover half and under and through the edge of the first cover half for carrying the first and second threads over the edge of the second cover half and under and through the edge of the first cover half, prior to said step of advancing the first and second needles in an opposite direction, holding the second thread between the first and second needles and above the first needle;
releasing the second thread upon passage of the first needle under the second thread; and
repeating said steps of advancing, holding and releasing for shuttling the first and second thread carrying needles back and forth over and under and through the edges of the first and second cover halves to create a regular herringbone stitch pattern between the first and second cover halves as the cover is sewn around the ball core.

2. A method for sewing cover halves together around a ball core as defined in claim 1 wherein said steps of advancing the first and second needles in one direction and then in an opposite direction each comprise the steps of:
pushing the first and second needles alternately at each end to project the needles at least partially through the edges of the cover halves; and
catching and pulling the first and second needles alternately at the opposite ends to pull the needles completely through the edges of the cover halves whereby a back and forth stitching action of the first and second needles is provided.

3. A method for sewing cover halves together around a ball core as defined in claim 2 wherein said steps of advancing the first and second needles further comprise the step of:
advancing the first and second needles abreast and in parallel planes in a back and forth shuttle mode.

4. A method for sewing cover halves together around a ball core as defined in claim 3 and further comprising the step of:
guiding the first and second needle tips alternately back and forth through both edges of the cover halves to be sewn around the ball core.

5. A method for sewing cover halves together around a ball core as defined in claim 2 and further comprising the step of:
advancing the cover halves an increment approximately equal to the lateral spacing between the first and second needles with each pass of the first and second needles through an edge of either of the cover halves.

6. A method for sewing cover halves together around a ball core as defined in claim 5 wherein said step of advancing comprises:
engaging thread receiving apertures preformed about the periphery of the cover halves with a wheel having tips for projection into the apertures; and
rotating the wheel for advancing the cover halves the distance between adjacent apertures for each transverse pass of the first and second needles.

7. A method for sewing cover halves together around a ball core as defined in claim 2 and following said steps of pulling the needles through each cover half the further steps of:
pulling the threads through each cover half; and
applying tension to the threads to pull the adjacent edges of the cover halves together.

8. A method for sewing cover halves together around a ball core as defined in claim 7 and in cooperation with said step of applying tension to the thread the step of:
releasably storing any excess length of thread between the first and second needles and the cover halves until the next sequential step of pulling the threads through a cover half.

9. A method for sewing cover halves together around a ball core as defined in claim 2 and prior to said step of pushing the first and second needles the steps of:
lowering an edge of the cover half adjacent to the advancing position of the first and second needles, and
raising an edge of the cover half opposite to the advancing position of the first and second needles for receiving advancing tips of the first and second needles.

10. A method for sewing cover halves together around a ball core as defined in claim 9 and further comprising the step of:
guiding the advancing tips of the first and second needles into thread receiving apertures preformed along each peripheral edge of each cover half.

11. An apparatus operable for sewing cover halves around a ball core comprising:
a frame;
a first needle having an aperture transversely extending therethrough and intermediate the ends thereof and for receiving a first thread;
a second needle having an aperture transversely extending therethrough and intermediate the ends thereof for receiving a second thread;
means operably connected to said frame for holding a ball core with first and second cover halves to be sewn together around said ball core in a posture adjacent to said first and second needles;
means operably connected to said frame for advancing said first and second needles in one direction over an edge of the first cover half and under and through an opposing edge of the second cover half for carrying the first and second threads over the edge of the first cover half and under and through the edge of the second cover half;
means operably connected to said frame for advancing said first and second needles in an opposite direction over the edge of the second cover half and under and through an opposing edge of the first cover half for carrying the first and second threads over the edge of the second cover half and under and through the edge of the first cover half, said first and second means for advancing being operable for carrying said first and second needles back and forth in a shuttle mode over and under and through the edges of the first and second cover halves; and
means operably connected to said frame for holding the second thread between said first and second needles and above said first needle when said first and second needles are advancing in an opposite direction to create a regular herringbone stitch pattern between the first and second cover halves of the cover being sewn around the ball core.

12. An apparatus operable for sewing cover halves around a ball core as defined in claim 11 wherein said means for advancing said first and second needles in one direction and said means for advancing said first and second needles in an opposite direction comprises:
first arm means for selectively engaging one of the ends of said first and second needles for pushing said needles in a first direction and pulling said needles in an opposite direction; and
second arm means for engaging the other of the ends of said first and second needles for pulling said needles in the first direction and pushing said needles in the opposite direction.

13. An apparatus operable for sewing cover halves around a ball core as defined in claim 12 wherein:
said first and second needles are each provided with transverse apertures adjacent each of the ends of said needles; and
said first and second arm means each being provided with transversely actuatable pin means for selectively engaging said apertures in the ends of said first and second needles for selectively pushing and pulling said needles with respect to the cover halves to be sewn around ball core.

14. An apparatus operable for sewing cover halves around a ball core as defined in claim 12 wherein:
said first and second arm means being operable for holding said needles in a mutually parallel posture and for advancing said needles in unison and abreast toward and away from the cover halves to be sewn around the ball core.

15. An apparatus operable for sewing cover halves around a ball core as defined in claim 14 and further comprising:
means operably connected to said frame for guiding said first and second needles in a parallel posture through each edge of the cover halves to be sewn around the ball core.

16. An apparatus operable for sewing cover halves around a ball core as defined in claim 12 wherein each cover half to be sewn around the ball core is formed with thread receiving apertures about the peripheral edges thereof and said apparatus further comprises:
means operably connected to said frame for engaging the thread receiving apertures in the cover halves and indexing the cover half apertures into alignment with said first and second needles wherein said needles engage adjacent pairs of apertures alternately in one direction and then the other and said means for engaging and indexing advances the cover halves one aperture position with each pass of said first and second needles.

17. An apparatus operable for sewing cover halves around a ball core as defined in claim 16 wherein said means for engaging and indexing comprises:
wheel means having radial projections with tips operable to engage with the thread receiving apertures in the cover halves; and
means for selectively driving said wheel means a distance approximately equal to the distance between adjacent apertures in the edge of said cover halves with each pass of said first and second needles.

18. An apparatus operable for sewing cover halves around a ball core as defined in claim 12 and further comprising:
means operably connected to said frame for pulling the first and second threads through the cover halves following passage of said first and second needles and tensioning the first and second threads to draw opposing edge portions to the cover halves together as the first and second needles shuttle back and forth sewing the ball cover halves around the ball core.

19. An apparatus operable for sewing cover halves around a ball core as defined in claim 18 and further comprising:
means operably connected to said frame for handling and storing the first and second threads in a controlled posture following each thread tensioning operation by said means for pulling and tensioning.

20. An apparatus operable for sewing cover halves around a ball core as defined in claim 19 wherein said means for handling and storing threads comprises:

at least one generally U-shaped elongate channel having flexible bristles affixed to interior arm surfaces of the U-shaped channel wherein the free ends of said bristles project in a mutually opposed and contiguous posture to engage and releasably retain the first and second threads between the tips of said bristles.

21. An apparatus operable for sewing cover halves on a ball core as defined in claim 12 and further comprising:

means operably connected to said frame for alternately raising and lowering the peripheral edges of the first and second cover halves for facilitating advancement of said first and second needles back and forth through the edges of the cover halves.

* * * * *